(12) United States Patent
Allef et al.

(10) Patent No.: US 7,910,119 B2
(45) Date of Patent: Mar. 22, 2011

(54) COSMETIC EMULSIONS WITH LONG-TERM STABILITY

(75) Inventors: Petra Allef, Bonn (DE); Peter Hameyer, Essen (DE); Jürgen Meyer, Münster (DE); Gabriele Polak, Hagen (DE)

(73) Assignee: Evonik Goldschmidt GmbH, Essen (DE)

( * ) Notice: Subject to any disclaimer, the term of this patent is extended or adjusted under 35 U.S.C. 154(b) by 486 days.

(21) Appl. No.: 11/369,566

(22) Filed: Mar. 7, 2006

(65) Prior Publication Data

US 2006/0204468 A1      Sep. 14, 2006

(30) Foreign Application Priority Data

Mar. 11, 2005   (DE) .......................... 10 2005 011 785

(51) Int. Cl.
 *A61K 8/02*      (2006.01)
(52) U.S. Cl. ...................................... 424/401; 514/938
(58) Field of Classification Search ............... 424/401; 514/938
 See application file for complete search history.

(56) References Cited

U.S. PATENT DOCUMENTS

| | | | | |
|---|---|---|---|---|
| 5,674,475 A | * | 10/1997 | Dahms et al. | 424/59 |
| 6,488,946 B1 | * | 12/2002 | Milius et al. | 424/401 |
| 2003/0138478 A1 | * | 7/2003 | Weuthen et al. | 424/443 |

FOREIGN PATENT DOCUMENTS

| | | |
|---|---|---|
| WO | WO 94/09753 | 5/1994 |
| WO | WO 00/04230 | 1/2000 |
| WO | WO 02/056841 | 7/2002 |

OTHER PUBLICATIONS

Shinoda, Kozo et al. "Phase Properties of Emulsions: PIT and HLB" *Emulsions, Microemulsions, and Solubilization*, p. 337-367 (1979).
Förster, Th. et al. "Production of Fine Disperse and Long-Term Stable Oil-In-Water Emulsions by the Phase Inversion Temperature Method" *J. Dispersion Science and Technology*, 13 (2), p. 183-193 (1992).
Finkel, P. et al. "Formulierung Kosmetischer Sonnenschutzmittel" *SÖFW-Journal*, 122 (1996).

* cited by examiner

*Primary Examiner* — Sreeni Padmanabhan
*Assistant Examiner* — Renee Claytor
(74) *Attorney, Agent, or Firm* — Scully, Scott, Murphy & Presser, P.C.

(57) ABSTRACT

Low-viscosity, finely divided oil-in-water emulsions with long-term stability, comprising an emulsifier combination of noncarbohydrate polyol partial esters of linear or branched, saturated or unsaturated fatty acids having 6 to 22 carbon atoms (emulsifier component A) and emulsifiers based on carbohydrate (emulsifier component B), one or more oils, and preservative are provided. Additionally, the present invention provides for the preparation of the emulsions from concentrates, the corresponding concentrates, and the use of the emulsions according to the invention for producing cosmetic, dermatological or pharmaceutical preparations, in particular for producing impregnation emulsions for wet wipes.

21 Claims, No Drawings

COSMETIC EMULSIONS WITH LONG-TERM STABILITY

FIELD OF THE DESCRIPTION

The present invention relates to low-viscosity, finely divided oil-in-water (O/W) emulsions with long-term stability, to their preparation from concentrates, to the corresponding concentrates, and to the use of the emulsions according to the invention for producing cosmetic, dermatological or pharmaceutical preparations, in particular for producing impregnation emulsions for wet wipes.

BACKGROUND OF THE INVENTION

Emulsions are an important product type in the field of cosmetic, dermatological and/or pharmaceutical preparations. Cosmetic preparations are essentially used for skincare. Skincare, in the cosmetics sense, refers to instances in which the natural function of the skin, as a barrier against environmental influences (for example dirt, chemicals, microorganisms) and against the loss of endogenous substances (for example water, natural fats, electrolytes), is strengthened or restored. Impairment of this function can lead to increased absorption of toxic or allergic substances or to attack by microorganisms and consequently to toxic or allergic skin reactions.

One aim of skincare is also to replenish the loss of fat and water from the skin caused by daily washing and to obtain and/or restore the softness and smoothness of the skin. This is especially important if the natural regeneration ability is inadequate. Furthermore, skincare products should protect against environmental effects, in particular against sun and wind, and delay skin aging. The sum of these skincare effects is generally summarized in cosmetics under the term "skin conditioning".

Cosmetic preparations are also used as deodorants. Pharmaceutical topical compositions generally comprise one or more medicaments in an effective concentration. For the sake of simplicity, and for a clear distinction between cosmetic and medicinal use and corresponding products, reference is made to the legal provisions of the Federal Republic of Germany (for example Cosmetics Directive, Foods and Drugs Act).

In recent years, cosmetic wet wipes have gained increasing importance due to their exceptionally easy and convenient usability. Initially, wet wipes for cleansing purposes were almost exclusively represented in the cosmetics market; these comprised primarily aqueous, surface-active impregnation solutions. More and more, however, care products are also appearing on the market; these are based on impregnation emulsions and thus additionally comprise a caring oil component.

Most of these cosmetic wet wipes for body care and face care are impregnated with emulsions which have been prepared by the PIT emulsification method (K. Shinoda, H. Kunieda, Phase properties of emulsions: PIT and HLB, Encycl. of Emulsion Technology, 337-367 (1), 1983 or Th. Förster, F. Schambil, W. von Rybinski, J. Disp. Sci. and Technology, 13(2), 183-93 (1992)). The PIT method makes use of the fact that, in an oil-in-water (O/W) emulsion which is stabilized by nonionic emulsifiers comprising polyethylene glycol, it is possible to induce a phase inversion to a water-in-oil (W/O) emulsion by increasing the temperature (phase inversion; PIT: phase inversion temperature). Since the water-oil interfacial tension is extremely low in this phase inversion range, extremely finely divided oil-in-water emulsions can thus be obtained after cooling. For this, however, it is necessary for the individual components of the emulsions to be precisely matched to one another for each system to be emulsified. This means emulsifier mixtures and emulsifier concentration have to "be tailored" for different oil phases.

Finely divided and low-viscosity emulsions prepared in the foregoing manner have excellent long-term stability and are thus readily suitable as impregnation solutions for wet wipes. Systems of this type are described, for example, in EP-B-1 268 740 or in WO-A-00/04230.

A commercially supplied emulsion concentrate, which is prepared using PIT technology, is Emulgade® CM from Cognis (Düsseldorf) which is based on the ethoxylated emulsifiers ceteareth-20 and ceteareth-12 and comprises cetyl isononanoate as an oil component. This concentrate can be diluted with water to the desired use concentration. The dilute emulsion can then be used as an impregnation solution for wet wipes.

A disadvantage of these prior art impregnation solutions for wet wipes based on PIT emulsions is that they comprise ethoxylated emulsifiers. In the course of cosmetic formulations which are as natural as possible, an important aim of cosmetics research is to be able to dispense with emulsifiers comprising polyethylene glycol ("PEG"). For this reason, the search for PEG-free alternative solutions has increased.

It is also known that ethoxylated emulsifiers impart a rather aqueous feel to the skin, which has to be improved in sensory terms through the use of, for example, polyglycerol esters.

For example, WO-A-02/056841 describes PEG-free impregnation emulsions for cosmetic wet wipes based on polyol poly-12-hydroxystearates and alkyl glycosides. A commercially available combination of these emulsifiers for the described purpose is the product Eumulgin® VL 75 (Cognis). The use of these emulsifier mixtures leads to an improved soft feel of paper products that are impregnated therewith and also leads to improved sensory properties when using the wet wipes produced therewith.

When producing wet wipes, adequate preservation of the impregnation solutions is very important in order to prevent the build-up of germs. Here, the preservation has to be sufficient that both the impregnation solutions themselves, and ultimately also the impregnated wet wipes are protected against the build-up of germs.

Preferred preserving mixtures used for this purpose in impregnation solutions are typically mixtures of alkyl paraben esters and phenoxyethanol, as are commercially available, for example under the trade names Euxyl® K 300 (Schülke & Mayr) and Phenonip® (Clariant).

The described high requirements with regard to reliable preservation of impregnation solution and wet wipes make it necessary for relatively large amounts of these alkyl paraben ester/phenoxyethanol mixtures to generally be used in the finished impregnation solutions (0.5 to 1.0% by weight). Ideally, the total amount of preservative should be incorporated when producing emulsion concentrates. This means that it is possible to simply establish the desired use concentration of the impregnation solution through dilution with water.

If one considers that the oil phase content of impregnation solutions is typically in the range from 3 to 10% by weight, then it will be appreciated that in 50 to 80% strength concentrates, approximately 5 to 15% by weight of Euxyl® K 300 or Phenonip® have to be present in order to ensure adequate preservation.

It is known that the use of these alkyl paraben ester/phenoxyethanol mixtures has an effect which is detrimental to the emulsion since these compounds are very interface-active and compete with emulsifier molecules for a place at the oil-water interface.

This detrimental effect on the emulsion is exacerbated in the case of impregnation emulsions for wet wipes as a result of the large amounts of these preservatives required and the low viscosities of the impregnation solutions. This makes the production of stable finely divided emulsions, which comprise adequate amounts of preservatives, very difficult.

Thus, it was found, for example, that, using the emulsifier combination described in WO-A-02/056841 (e.g. Eumulgin® VL 75) and incorporating the required amounts of the specified preservatives, it was not possible to obtain impregnation solutions with adequate stability (see comparative examples).

There is thus a continued need to provide PEG-free emulsifier systems which permit the formulation of impregnation solutions for producing cosmetic wet care wipes with an adequate amount of preservative. In addition, the emulsifier systems should permit the formulation of a large number of different oils.

SUMMARY OF THE INVENTION

Surprisingly, it has now been found that by combining emulsifiers based on polyglycerol with emulsifiers based on carbohydrate, it is possible to obtain finely divided and low-viscosity PEG-free emulsions which, even with the required amounts of preservatives, in particular alkyl paraben ester/phenoxyethanol, have excellent long-term stability and storage stability. Moreover, these emulsions are exceptionally suitable for producing impregnation solutions for wet care wipes. In particular, the inventive emulsions are characterized by their simple preparation and their fine degree of dispersion.

The wet wipes produced with the help of these impregnation solutions have a pleasant soft feel and, moreover, are characterized by extremely pleasant sensory properties.

The present invention provides an oil-in-water emulsion comprising an emulsifier combination of noncarbohydrate polyol partial esters of linear or branched, saturated or unsaturated fatty acids having 6 to 22 carbon atoms (emulsifier component A) and emulsifiers based on carbohydrate (emulsifier component B), one or more oils, at least 10% by weight of preservative, based on the total amount of emulsifier components A and B.

With the oil-in-water emulsion according to the present invention, a PEG-free, low-viscosity emulsion is available for the first time which, despite a high content of preservatives, has long-term stability and is thus suitable for use as, for example, impregnation emulsion for wet wipes.

The invention therefore further provides a PEG-free oil-in-water emulsion (i.e., one comprising no ethoxylated constituents) comprising an emulsifier combination of noncarbohydrate polyol partial esters of linear or branched fatty acids having 6 to 22 carbon atoms (emulsifier component A) and emulsifiers based on carbohydrate (emulsifier component B), one or more oils and preservative.

DETAILED DESCRIPTION OF THE INVENTION

As stated above in the previous section of the instant application, the present application provides an oil-in-water emulsion comprising an emulsifier combination of noncarbohydrate polyol partial esters of linear or branched, saturated or unsaturated fatty acids having 6 to 22 carbon atoms (emulsifier component A) and emulsifiers based on carbohydrate (emulsifier component B), one or more oils, at least 10% by weight of preservative, based on the total amount of emulsifier components A and B. The 'essential' components of the present invention as well as any optional components will now be described in greater detail.

In accordance with the present invention, carbohydrates are defined as polyhydroxyaldehydes (aldoses) and polyhydroxyketones (ketoses), and higher molecular weight compounds which can be converted into such compounds by hydrolysis. The carbohydrates mostly have the net formula $C_nH_{2n}O_n$ or $C_n(H_2O)_n$. The monomeric polyhydroxyaldehydes or polyhydroxyketones are referred to as monosaccharides, their dimers to decamers as oligosaccharides (disaccharides, trisaccharides, etc.) and the macromolecular carbohydrates as polysaccharides. The mono- and oligosaccharides are grouped together as "sugars" and differentiated from the polysaccharides.

The monosaccharides exhibit the following common reaction: copper salts, silver salts and bismuth salts are reduced in solution, hydrocyanic acid is added, with phenylhydrazine osazones are formed.

For the purposes of the present invention, noncarbohydrates are therefore polyols which do not correspond to the definition of carbohydrates and do not exhibit their reaction. Some of the polyols which can be co-used according to the invention can, however, be prepared from them by reduction, such as, for example, the sugar alcohols or anhydrides thereof such as, for example, sorbitans (monoanhydrosorbites).

The oil-in-water emulsion according to the invention preferably comprises 20 to 75% by weight of preservative, based on the total amount of emulsifier components A and B.

The oil-in-water emulsions according to the present invention can additionally optionally comprise coemulsifiers and customary auxiliaries and additives.

The emulsifier component A of the present invention preferably is exclusively or partly polyglycerol partial esters which are obtainable, for example, by reacting polyglycerols with linear or branched fatty acids having 6 to 22 carbon atoms. The polyglycerol mixture used advantageously has an average degree of condensation of from 2 to 10, preferably from 2 to 8 and particularly preferably from 3 to 6.

The degree of esterification of the polyglycerol mixture used in the present invention is advantageously between 5 and 70%, preferably between 10 and 30%, based on the original hydroxyl groups of the polyol.

If desired, the emulsifier component A can be formed partly or completely, for example, by sorbitan mono- and/or diesters of unsaturated and saturated fatty acids having 6 to 22 carbon atoms. Preference is given in this invention to using sorbitan monooleate (for example, the commercial product TEGO® SMO V).

Preferably, emulsifier component A can comprise, besides one or more polyglycerol partial esters, up to 50% by weight of sorbitan esters, based on the total amount of emulsifier component A. Depending on the oil system, even an exclusive use of sorbitan ester as emulsifier component A is sometimes preferred. However, this may also lead to less finely divided impregnation emulsions.

Emulsifier component B is one or more different emulsifiers based on carbohydrate which are preferably chosen from the following groups:

i) Esters of mono- and/or polysaccharides and one or more linear or branched fatty acids having 6 to 22 carbon atoms.

ii) Glycosides of mono- or polysaccharides and linear or branched fatty alcohols having 6 to 22 carbon atoms. Examples of such products are alkyl polyglycosides, such as 1-octyl-, 1-decyl-, 1-lauryl-, 1-myristyl-, 1-cetyl- and 1-stearylalkyl polyglycoside. The fatty alcohols are typically, but not necessarily always, obtained from natural fats and oils, as a result of which a distribution of different alkyl chains alongside one another may be present. Besides the alkyl radicals, or instead of them, it is also possible to use alkenyl radicals. The alkyl polyglycosides used according to the invention comprise, on average, preferably 1 to 5 sugar units, particularly preferably 1.1 to 2 sugar units.

iii) Glycosides which have additionally been etherified with linear or branched fatty alcohols having 1 to 22 carbon atoms. The fatty alcohols are typically, but not necessarily always, obtained from natural fats and oils, as a result of which a distribution of different chain lengths alongside one another may be present.

iv) Glycoside esters of mono- or polysaccharides and linear or branched fatty alcohols having 1 to 22 carbon atoms and one or more linear or branched fatty acids having 1 to 22 carbon atoms. Here, both fatty acids and also fatty alcohols can be obtained from natural fats and oils and thus have a chain length distribution.

Any mono- or oligosaccharides may be used as a sugar building block. Sugars with 5 or 6 carbon atoms, and also the corresponding oligosaccharides, are usually used. Such sugars may, for example, be glucose, fructose, galactose, arabinose, ribose, xylose, lyxose, allose, altrose, mannose, gulose, idose, talose and sucrose.

The fatty acid component used in the present invention is preferably caprylic acid, heptanoic acid, capric acid, nonanoic acid, isononanoic acid, lauric acid, tridecanoic acid, myristic acid, palmitic acid, stearic acid, isostearic acid, arachidic acid and behenic acid, and mixtures thereof. Naturally occurring mixtures are, for example, the coconut fatty acids which comprise, as a main constituent, lauric acid, as well as saturated $C_{14}$- to $C_{18}$-fatty acids and optionally saturated $C_8$- to $C_{10}$-fatty acids and unsaturated fatty acids, and also tallow fatty acids, which essentially represent a mixture of palmitic acid and stearic acid.

Suitable additional unsaturated fatty acid components are monoolefinically unsaturated acids, for example, hexadecenoic acids, octadecenoic acids, such as oleic acid (cis-9-octadecenoic acid) or elaidic acid (trans-9-octadecenoic acid), eicosenoic acids and docosenoic acids, such as erucic acid (cis-13-docosenoic acid) or brassidic acid (trans-13-docosenoic acid), polyunsaturated fatty acids, for example octadecadienoic acids and octadecatrienoic acids, such as linoleic acid and linolenic acid, and mixtures thereof.

Likewise suitable are the fatty acids which are liquid at room temperature, such as oleic acid, ricinoleic acid, erucic acid and isostearic acid, which comprise 18 to 22 carbon atoms. Their solidification points are below 35° C. on account of branching or a double bond in the hydrocarbon chain. It is also possible to use fatty acid mixtures, which may also comprise wax-like components, such as hydrogenated ricinoleic acid.

The alcohol component used in the present invention is preferably: methanol, ethanol, propanol, isopropanol, butanol, pentanol, hexanol, heptanol, octanol, nonanol, isononyl alcohol, decanol, lauryl alcohol, myristyl alcohol, cetyl alcohol, or stearyl alcohol. Likewise of suitability are unsaturated fatty alcohols, such as oleyl alcohol, and branched alcohols, such as Guerbet alcohol.

In accordance with the present invention, the emulsifier components A and B are used in a weight ratio of from 9:1 to 1:9, preferably from 8:2 to 2:8 and particularly preferably from 7:3 to 3:7, with approximate parity in the range from 3:2 to 2:3 or 5:4 to 4:5 being optimal.

The total amount of the emulsifier components A+B used in the present invention ranges, preferably based on the amount of oil to be emulsified, within a range from 15 to 70% by weight, preferably from 25 to 55% by weight and particularly preferably from 30 to 50% by weight.

Suitable preservatives used are particularly preferably mixtures of individual or a plurality of alkyl paraben esters with phenoxyethanol. The alkyl paraben esters are preferably methyl paraben, ethyl paraben, propyl paraben and/or butyl paraben, or alkoxides thereof, in particular sodium alkoxylates. Instead of phenoxyethanol it is also possible to use other alcohols, such as, for example, benzyl alcohol or ethanol.

Moreover, it is also possible to use other customary preservatives such as, for example, sorbic acid or benzoic acid, salicylic acid, 2-bromo-2-nitropropane-1,3-diol, chloroacetamide, diazolidinylurea, DMDM hydantoin, iodopropynyl butylcarbamate, sodium hydroxymethylglycinate or the combination chloromethyl-/methylisothiazoline.

With fractions of at least 10% by weight of preservatives, adequate preservation can generally be achieved. According to the invention, preference is given to concentrations that are ≧20% by weight to about 75% by weight. Higher fractions are possible, but not preferable for the reasons specified above.

Oils present in the oil-in-water emulsion according to the invention may, for example, be cosmetic oils. Suitable cosmetic oils are, in particular, mono- or diesters of linear and/or branched mono- and/or dicarboxylic acids having 2 to 44 carbon atoms with linear and/or branched saturated or unsaturated alcohols having 1 to 22 carbon atoms. In one embodiment of the invention, the esterification products of aliphatic, difunctional alcohols having 2 to 36 carbon atoms with monofunctional aliphatic carboxylic acids having 1 to 22 carbon atoms are likewise suitable. Monoesters suitable as oil components are, for example, the methyl esters and isopropyl esters of fatty acids having 12 to 22 carbon atoms, such as, for example, methyl laurate, methyl stearate, methyl oleate, methyl erucate, isopropyl palmitate, isopropyl myristate, isopropyl stearate, or isopropyl oleate. Other suitable monoesters are, for example, n-butyl stearate, n-hexyl laurate, n-decyl oleate, isooctyl stearate, isononyl palmitate, isononyl isononanoate, 2-ethylhexyl palmitate, 2-ethylhexyl laurate, 2-hexyldecyl stearate, 2-octyldodecyl palmitate, oleyl oleate, oleyl erucate, erucyl oleate, and esters which are obtainable from technical-grade aliphatic alcohol cuts and technical-grade aliphatic carboxylic acid mixtures, for example esters of unsaturated fatty alcohols having 12 to 22 carbon atoms and saturated and unsaturated fatty acids having 12 to 22 carbon atoms, as are accessible from animal and vegetable fats. Also of suitability are, naturally occurring monoester or wax ester mixtures, as are present, for example, in jojoba oil or in sperm oil.

Suitable dicarboxylic acid esters are, for example, di-n-butyl adipate, di-n-butyl sebacate, di(2-ethylhexyl) adipate, di(2-hexyldecyl) succinate, diisotridecyl acelate. Suitable diol esters are, for example, ethylene glycol dioleate, ethylene glycol diisotridecanoate, propylene glycol di(2-ethylhexanoate), butanediol diisostearate and neopentyl glycol dicaprylate. In addition, esters of benzoic acid, such as $C_{12-15}$-alkyl benzoate and also carbonates, preferably dialkyl carbonates, such as dicaprylyl carbonate, diethylhexyl carbonate and diisononyl carbonate, can be used.

As oil component it is likewise possible to use fatty acid triglycerides, preference being given among these to the naturally occurring oils and fats. Thus, for example, natural vegetable oils, for example olive oil, sunflower oil, soya oil, peanut oil, rapeseed oil, almond oil, or palm oil, but also the liquid fractions of coconut oil or of palm kernel oil, and animal oils, such as, for example, neatsfoot oil, the liquid fractions of beef tallow or also synthetic triglycerides of caprylic/capric acid mixtures, triglycerides of technical-grade oleic acid or of palmitic acid/oleic acid mixtures are suitable as oil components. In addition, hydrocarbons, in particular also liquid paraffins and isoparaffins, can be used. Furthermore, fatty alcohols such as oleyl alcohol or octyldodecanol, and also fatty alcohol ethers, such as dicaprylyl ether, can also be used. Suitable silicone oils and silicone waxes are, for example, polydimethylsiloxanes, cyclomethylsiloxanes, and also aryl- or alkyl- or alkoxy-substituted polymethylsiloxanes or cyclomethylsiloxanes, in which case these silicone oils should constitute not more than 50% by weight of the oil phase used.

Particularly preferred oil components are the cosmetic ester oils ethylhexyl palmitate, ethylhexyl stearate, decyl cocoate, diethylhexyl carbonate, dioctyl carbonate, cetearyl ethylhexanoate, cetearyl isononanoate, hexyl laurate, isopropyl isononanoate, isopropyl palmitate, isopropyl myristate and isopropyl laurate.

Overall, the formulations according to the invention can advantageously comprise 1 to 25% by weight of oil phase (oil+emulsifier), in particular 1.5 to 10% by weight of oil phase and particularly preferably 2 to 6% by weight of oil phase.

Besides the emulsifier components described, further emulsifiers or surfactants may be present in the emulsions according to the invention. These are preferably nonionic, anionic, cationic or amphoteric surfactants.

Suitable nonionogenic surfactants are compounds from at least one of the following groups:
 addition products of from 2 to 30 mol of ethylene oxide and/or 0 to 5 mol of propylene oxide onto linear fatty alcohols having 8 to 22 carbon atoms, onto fatty acids having 12 to 22 carbon atoms and onto alkylphenols having 8 to 15 carbon atoms in the alkyl group,
 $C_{12}/_{18}$-fatty acid mono- and diesters of addition products of from 1 to 30 mol of ethylene oxide onto glycerol,
 glycerol mono- and diesters and sorbitan mono- and diesters of saturated and unsaturated fatty acids having 6 to 22 carbon atoms and ethylene oxide addition products thereof,
 ethoxylated alkyl mono- and oligoglycosides having 8 to 22 carbon atoms in the alkyl radical,
 addition products of from 15 to 200 mol of ethylene oxide onto castor oil and/or hydrogenated castor oil,
 polyol and in particular polyglycerol esters, such as, for example, polyglycerol polyricinoleate, polyglycerol poly-12-hydroxystearate or polyglycerol dimerate. Mixtures of compounds from two or more of these classes of substances are likewise suitable,
 addition products of from 2 to 15 mol of ethylene oxide onto castor oil and/or hydrogenated castor oil,
 partial esters based on linear, branched, unsaturated or saturated $C_{6/22}$-fatty acids, ricinoleic acid, and 12-hydroxystearic acid and glycerol, polyglycerol, pentaerythritol, dipentaerythritol, sugar alcohols (for example sorbitol), alkyl glucosides (for example methyl glucoside, butyl glucoside, lauryl glucoside), and polyglucosides (for example cellulose),
 mono-, di- and trialkyl phosphates, and mono-, di- and/or tri-PEG alkyl phosphates and salts thereof,
 polysiloxane-polyether copolymers (dimethicone copolyols), such as, for example, PEG/PPG-20/6 dimethicone, PEG/PPG-20/20 dimethicone, bis-PEG/PPG-20/20 dimethicone, PEG-12 or PEG-14 dimethicone, PEG/PPG-14/4 or 14/12 or 20/20 or 18/18 or 17/18 or 15/15. Of particular suitability are products such as bis-PEG/PPG-14/14 dimethicone (with cyclopentasiloxane: ABIL® EM 97) or in particular PEG/PPG-16/16 dimethicone (with caprylic/capric triglycerides: ABIL® Care 85),
 polysiloxane-polyalkyl-polyether copolymers and corresponding derivatives, such as, for example, lauryl or cetyl dimethicone copolyols, in particular cetyl PEG/PPG-10/1 dimethicone (ABIL® EM 90),
 mixed esters of pentaerythritol, fatty acids, citric acid and fatty alcohol according to DE-B 11 65 574 and/or mixed esters of fatty acids having 6 to 22 carbon atoms, methylglucose and polyols, preferably glycerol or polyglycerol.

It is also possible to additionally use anionic surfactants. These contain water-solubilizing anionic groups, such as, for example, a carboxylate, sulfate, sulfonate or phosphate group and a lipophilic radical. Skin-compatible anionic surfactants are known to the person skilled in the art in large numbers and are commercially available. These are, in particular, alkyl sulfates or alkyl phosphates in the form of their alkali metal, ammonium or alkanolammonium salts, alkyl ether sulfates, alkyl ether carboxylates, acyl sarcosinates, and sulfosuccinates and acyl glutamates in the form of their alkali metal or ammonium salts.

Cationic surfactants can also be added. As such, it is possible to use, in particular, quaternary ammonium compounds, such as alkyltrimethylammonium halides, such as, for example, cetyltrimethylammonium chloride or bromide or behenyltrimethylammonium chloride, but also dialkyldimethylammonium halides, such as, for example, distearyldimethylammonium chloride. In addition, monoalkylamidoquats, such as, for example, palmitamidopropyltrimethylammonium chloride or corresponding dialkylamidoquats can be used. In addition, it is also possible to use readily biodegradable quaternary ester compounds, which are mostly quaternized fatty acid esters based on mono-, di- or triethanolamine. Moreover, alkylguanidinium salts can be added as cationic emulsifiers.

The addition of these cationic surfactants to the compositions according to the invention can bring about a significant improvement in the soft feel of the wet care wipes.

In addition, it is possible to add amphoteric surfactants, such as, for example, betaines, amphoacetates or amphopropionates, to the compositions according to the invention.

In addition, the oil-in-water emulsions according to the invention can comprise customary auxiliaries and additives, such as consistency regulators, thickeners, waxes, UV photoprotective filters, antioxidants, hydrotropes, deodorant and antiperspirant active ingredients, insect repellents, self-tanning agents, perfume oils, dyes and biogenic active ingredients.

Suitable consistency regulators are primarily fatty alcohols or hydroxy fatty alcohols having 12 to 22 and preferably 16 to 18 carbon atoms and also partial glycerides, fatty acids or hydroxy fatty acids.

Suitable thickeners are, for example, polysaccharides, in particular xanthan gum, guar and guar derivatives, agar agar, alginates and tyloses, cellulose and cellulose derivatives, such as, for example, carboxymethylcellulose, hydroxyethylcellulose, hydroxymethylpropylcellulose, also alkyl-modified sugar derivatives, such as, for example, cetylhydroxyethylcellulose, also higher molecular weight polyethylene glycol mono- and diesters of fatty acids, carbomers (crosslinked polyacrylates), polyacrylamides, polyvinyl alcohol and polyvinylpyrrolidone, surfactants, such as, for example, ethoxylated fatty acid glycerides, esters of fatty acids with polyols, such as, for example, pentaerythritol or trimethylolpropane, fatty alcohol ethoxylates with a narrowed homolog distribution or alkyl oligoglucosides.

UV photoprotective filters which may be present in the emulsions according to the invention are understood as meaning organic substances which are able to absorb ultraviolet rays and give off the absorbed energy again in the form of longer-wave radiation, for example heat. UV-B filters which may be used may be oil-soluble or water-soluble. Examples of oil-soluble UV-B filters which may be used are:

3-benzylidenecamphor and derivatives thereof, for example 3-(4-methylbenzylidene)camphor,
4-aminobenzoic acid derivatives, preferably 2-ethylhexyl 4-(dimethylamino)benzoate, 2-ethylhexyl 4-(dimethylamino)benzoate and amyl 4-(dimethylamino)benzoate,
esters of cinnamic acid, preferably 2-ethylhexyl 4-methoxycinnamate, isopentyl 4-methoxycinnamate, 2-ethylhexyl 2-cyano-3-phenylcinnamate (octocrylene),
esters of salicylic acid, preferably 2-ethylhexyl salicylate, 4-isopropylbenzyl salicylate, homomenthyl salicylate,
derivatives of benzophenone, preferably 2-hydroxy-4-methoxybenzophenone, 2-hydroxy-4-methoxy-4'-methylbenzophenone, 2,2'-dihydroxy-4-methoxybenzophenone,
esters of benzalmalonic acid, preferably di-2-ethylhexyl 4-methoxybenzalmalonate,
triazine derivatives, such as, for example, 2,4,6-trianilino(p-carbo-2'-ethyl-1'-hexyloxy)-1,3,5-triazine and octyltriazone,
propane-1,3-diones, such as, for example, 1-(4-tert-butylphenyl)-3-(4'-methoxyphenyl)propane-1,3-dione.

Suitable water-soluble substances which can be used are:
2-phenylbenzimidazole-5-sulfonic acid and the alkali metal, alkaline earth metal, ammonium, alkylammonium, alkanolammonium and glucammonium salts thereof,
sulfonic acid derivatives of benzophenone, preferably 2-hydroxy-4-methoxybenzophenone-5-sulfonic acid and its salts,
sulfonic acid derivatives of 3-benzylidenecamphor, such as, for example, 4-(2-oxo-3-bornylidenemethyl)benzenesulfonic acid and 2-methyl-5-(2-oxo-3-bornylidene) sulfonic acid and salts thereof.

Suitable typical UV-A filters which can be used according to the invention are, in particular, derivatives of benzoylmethane, such as, for example, 1-(4'-tert-butylphenyl)-3-(4'-methoxyphenyl)propane-1,3-dione or 1-phenyl-3-(4'-isopropylphenyl)propane-1,3-dione. The UV-A and UV-B filters can of course also be used in mixtures. Besides the specified soluble substances, insoluble pigments are also suitable for this purpose, namely finely disperse metal oxides or salts, such as, for example, titanium dioxide, zinc oxide, iron oxide, aluminum oxide, cerium oxide, zirconium oxide, silicates (talc), barium sulfate and zinc stearate. The particles should have an average diameter of less than 100 nm, preferably between 5 and 50 nm and in particular between 15 and 30 nm. The particles can have a spherical shape, although it is also possible to use particles which have an ellipsoidal shape or a shape which deviates in some other way from the spherical configuration. A relatively new class of photoprotective filters are micronized organic pigments, such as, for example, 2,2'-methylenebis{6-(2H-benzotriazol-2-yl)-4-(1,1,3,3-tetramethylbutyl)phenol} with a particle size of less than 200 nm, which is obtainable, for example, as 50% strength aqueous dispersion.

Besides the two abovementioned groups of primary photoprotective substances, it is also possible to use secondary photoprotective agents of the antioxidant type; these interrupt the photochemical reaction chain which is triggered when UV radiation penetrates into the skin. Typical examples thereof are superoxide dismutase, tocopherols (vitamin E) and ascorbic acid (vitamin C). Further suitable UV photoprotective filters can be found in the overview by P. Finkel in SÖFW-Journal 122, 543 (1996).

To improve the flow behavior and the application properties, it is also possible to use hydrotropes, such as, for example, ethanol, isopropyl alcohol, or polyols. Polyols which are suitable here preferably have 2 to 15 carbon atoms and at least two hydroxyl groups. Typical examples are:

glycerol,
alkylene glycols, such as, for example, ethylene glycol, diethylene glycol, propylene glycol, butylene glycol, hexylene glycol, and polyethylene glycols with an average molecular weight of from 100 to 1000 daltons,
technical-grade oligoglycerol mixtures with a degree of self-condensation of from 1.5 to 10, such as, for example, technical-grade diglycerol mixtures with a diglycerol content of from 40 to 50% by weight,
methylol compounds, such as, in particular, trimethylolethane, trimethylolpropane, trimethylolbutane, pentaerythritol and dipentaerythritol,
lower alkyl glucosides, in particular those having 1 to 4 carbon atoms in the alkyl radical, such as, for example, methyl glucoside and butyl glucoside,
sugar alcohols having 5 to 12 carbon atoms, such as, for example, sorbitol or mannitol,
sugars having 5 to 12 carbon atoms, such as, for example, glucose or sucrose,
amino sugars, such as, for example, glucamine.

Suitable deodorant active ingredients are, for example, odor concealers, such as the customary perfume constituents, odor absorbers, for example the sheet silicates described in the patent laid-open specification DE-40 09 347, of these, in particular, montmorillonite, kaolinite, illite, beidelite, nontronite, saponite, hectorite, bentonite, smectite, also, for example, zinc salts of ricinoleic acid. Antibacterial agents are likewise suitable for incorporation into the oil-in-water emulsions according to the invention. Advantageous substances are, for example, 2,4,4'-trichloro-2'-hydroxydiphenyl ether (irgasan), 1,6-di(4-chlorophenylbiguanido)hexane (chlorhexidine), 3,4,4'-trichlorocarbanilide, quaternary ammonium compounds, oil of cloves, mint oil, thyme oil, triethyl citrate, farnesol (3,7,11-trimethyl-2,6,10-dodecatrien-1-ol), and the active agents described in the patent laid-open specifications DE-198 55 934, DE-37 40 186, DE-39 38 140, DE-42 04 321, DE42 29 707, DE42 29 737, DE42 38 081, DE43 09 372, DE-43 24 219 and EP-666 732. Further customary antiperspirant active ingredients can likewise be used advantageously in the preparations according to the invention, in particular astringents, for example basic aluminum chlorides, such as aluminum chlorohydrate ("ACH") and aluminum zirconium glycine salts ("ZAG").

Suitable insect repellents are N,N-diethyl-m-toluamide, 1,2-pentanediol or Insect Repellent 3535.

Suitable self-tanning agents are, for example, dihydroxyacetone and erythrulose.

Perfume oils which may be mentioned are mixtures of natural and synthetic fragrances. Natural fragrances are extracts from flowers (lily, lavender, rose, jasmine, neroli, ylang-ylang), stems and leaves (geranium, patchouli, petitgrain), fruits (anise, coriander, caraway, juniper), fruit peels (bergamot, lemons, oranges), roots (mace, angelica, celery, cardamom, costus, iris, thyme), needles and branches (spruce, fir, pine, dwarf-pine), resins and balsams (galbanum, elemi, benzoin, myrrh, olibanum, opoponax). Animal raw materials are also suitable, such as, for example, civet and castoreum. Typical synthetic fragrance compounds are products of the ester, ether, aldehyde, ketone, alcohol and hydrocarbon type. Fragrance compounds of the ester type are, for example, benzyl acetate, phenoxyethyl isobutyrate, p-tert-butyl cyclohexylacetate, linalyl acetate, dimethylbenzylcarbinyl acetate, phenylethyl acetate, linalyl benzoate, benzyl formate, ethylmethyl phenylglycinate, allyl cyclohexylpropionate, styrallyl propionate and benzyl salicylate. The ethers include, for example, benzyl ethyl ether, the aldehydes include, for example, the linear alkanals having 8 to 18 carbon atoms, citral, citronellal, citronellyloxyacetaldehyde, cyclamenaldehyde, hydroxycitronellal, lilial and bourgeonal, the ketones include, for example, the ionones, α-isomethylionone and methyl cedryl ketone, the alcohols include anethol, citronellol, eugenol, isoeugenol, geraniol, linalool, phenylethyl alcohol and terpineol, and the hydrocarbons include primarily the terpenes and balsams. However, preference is given to using mixtures of different fragrances which together produce a pleasing scent note. Essential oils of low volatility, which are mostly used as aroma components, are also suitable as perfume oils, for example sage oil, camomile oil, oil of cloves, melissa oil, mint oil, cinnamon leaf oil, linden blossom oil, juniper berry oil, vetiver oil, olibanum oil, galbanum oil, labdanum oil and lavandin oil. Preference is given to using bergamot oil, dihydromyrcenol, lilial, lyral, citronellol, phenylethyl alcohol, α-hexylcinnamaldehyde, geraniol, benzyl acetate, cyclamenaldehyde, lanalool, boisambrene forte, ambroxan, indol, hedione, sandelice, lemon oil, mandarin oil, orange oil, allyl amyl glycolate, cyclovertal, lavandin oil, clary sage oil, β-damascone, geranium oil bourbon, cyclohexyl salicylate, vertofix coeur, iso-E-Super, fixolide NP, evernyl, iraldein gamma, phenylacetic acid, geranyl acetate, benzyl acetate, rose oxide, romillat, irotyl and floramat alone or in mixtures.

Dyes which can be used are the substances which are approved and suitable for cosmetic purposes, as are listed, for example, in the publication "Kosmetische Färbemittel" [Cosmetic Colorants] from the Dyes Commission of the German Research Society, Verlag Chemie, Weinheim, 1984, pp. 81 to 106. These dyes are usually used in concentrations of from 0.001 to 0.1% by weight, based on the total mixture.

Biogenic active ingredients are understood as meaning, for example, tocopherol, tocopherol acetate, tocopherol palmitate, ascorbic acid, deoxyribonucleic acid, retinol, bisabolol, allantoin, phytantriol, panthenol, AHA acids, amino acids, hyaluronic acid, creatine (and creatine derivatives), guanidine (and guanidine derivatives), ceramides, phytosphingosine (and phytosphingosine derivatives), sphingosine (and sphingosine derivatives), pseudoceramides, essential oils, peptides, protein hydrolysates, plant extracts and vitamin complexes.

The invention further provides a method of preparing finely divided, low-viscosity oil-in-water emulsions with the composition described above, where firstly an emulsion concentrate is prepared at elevated temperatures and then diluted with water.

Thus, it has surprisingly been found that via the intermediate of a microemulsion-like concentrate which can be prepared at elevated temperatures with minimal stirring and by subsequent dilution of this concentrate, it is possible to obtain very finely divided emulsions which are characterized by excellent storage stability although relatively large amounts of alkyl paraben ester/phenoxyethanol are present as preservative.

In this connection, there was a clear tendency that only those emulsions which were capable of forming a transparent-clear or virtually transparent microemulsion-like phase at elevated temperatures as emulsion concentrate could be prepared in the form of a fine dispersion and thus with long-term stability.

Emulsions which have a milky-cloudy appearance at 40 to 60° C. no longer have long-term stability upon storage in the dilution to application concentration due to an excessively coarse degree of dispersion and lie outside of the invention.

The emulsion concentrates required as precursor for finely dispersed, low-viscosity emulsions can be prepared on a laboratory scale with the help of simple, manual stirring on a hotplate. The emulsion concentrates of the present invention comprise 10 to 70% by weight, preferably 20 to 50% by weight, of water; they are thus 30 to 90% strength, preferably 50 to 80% strength.

Typically, the emulsion concentrates according to the invention are prepared at temperatures between 40° and 85° C. by stirring the water phase in portions into the oil phase, which essentially consists of emulsifier mixture, oil and preservative. Perfume oils are typically added to this emulsion concentrate at about 40° C. They are generally solubilized to give a clear solution. Depending on the combination of emulsifier mixture, oil and amount of preservative and optionally auxiliaries and additives, with systems according to the invention transparent or virtually transparent microemulsion-like phases are observed in one part of the temperature range described above, in particular in the range from 50° to 65° C.

These emulsion concentrates are not storage-stable on cooling (phase separation) and therefore have to be diluted at the latest at the lower temperature limit of the microemulsion-like range. In this connection, it is advantageous to dilute the emulsion concentrates by stirring them into an initial charge of water whose temperature should be no more than 15° C. lower than the lower temperature limit of the microemulsion-like range. Preferably, the emulsion concentrates described are diluted by stirring them into an initially charged water phase of from 20° to 50° C.

In this connection, there was a clear tendency that only those emulsions which were able to form a transparent-clear or virtually transparent microemulsion-like phase at elevated temperatures as emulsion concentrate could be prepared in a finely disperse form and thus have long-term stability.

Emulsions which have a milky-cloudy appearance at 40° to 60° C. no longer have long-term stability upon storage in the dilution to application concentration due to an excessively coarse degree of dispersion and lie outside of the invention.

For the purposes of the invention, long-term stability means that the emulsions can be stored for 3 months at room temperature (25° C.) and about 1 month at 40° C. without recognizable or noteworthy phase separation.

The invention therefore further provides an essentially transparent concentrate in the range from 50° to 65° C., comprising 30 to 90% by weight, particularly preferably 50 to 80% by weight, of an oil phase, consisting essentially of oil component, emulsifier components and preservative and ad 100% by weight of a water phase, where the concentrate is essentially PEG-free.

The invention further provides the use of the emulsions according to the invention for producing cosmetic, dermatological or pharmaceutical preparations. In particular, the use as impregnation solutions for producing wet wipes, more particularly, cosmetic wet wipes for the care and cleansing of the skin is at the fore.

The invention further provides the use of the emulsions for producing cosmetic cleansing and care preparations for skin and skin appendages.

The invention further provides the use of the emulsions for producing sunscreen formulations and self-tanning preparations, which preferably comprise dihydroxyacetone or erythrulose. In particular, the use as impregnation solutions for producing cosmetic wet wipes for sun protection or for self-tanning applications is at the fore.

The invention further provides the use of the emulsions for producing cleaning and care compositions for hard surfaces. In particular, the use as impregnation solutions for producing wet wipes for the care and cleaning of hard surfaces is at the fore.

The following example emulsions are intended to illustrate the subject-matter of the invention in more detail without limiting it to these examples.

The concentrations given in all of the examples are % by weight.

In all of the use examples, the perfume oils were added to the emulsion concentrates at 40 to 45° C. before they were diluted with water.

For a better understanding, the emulsion concentrates prepared as intermediates during production are shown in addition to the impregnation emulsions which can be prepared therefrom.

It can be seen that even during the preparation of the emulsion concentrates it was possible to recognize whether ultimately stable impregnation emulsions could be formulated. If extremely finely divided, microemulsion-like (ME-like) emulsion concentrates were not obtained, then stable impregnation emulsions cannot be prepared either from them by dilution.

The methyl glucose sesquistearate used in the emulsions corresponds to the commercially available product TEGO® Care PS (Degussa).

The polyglyceryl-4 laurate used was prepared by reacting polyglycerol with an average degree of condensation of 4 and lauric acid. The average degree of esterification of the polyglycerol was 15%.

|   |   | Emulsion concentrate | | | | |
|---|---|---|---|---|---|---|
|   |   | 1a Comparative example | 2a Comparative example | 3a | 4a | 5a |
| A | Polyglyceryl-2 dipolyhydroxystearate | 8.0% | 7.0% |   |   |   |
|   | Lauryl glucoside | 8.0% | 7.0% |   |   |   |
|   | Methyl glucose sesquistearate |   |   | 8.0% | 7.5% | 7.0% |
|   | Polyglyceryl-4 laurate |   |   | 8.0% | 7.5% | 7.0% |
|   | Ethylhexyl palmitate | 48.0% | 42.0% | 48.0% | 45.0% | 42.0% |
|   | Phenonip ® | 9.0% | 8.0% | 9.0% | 8.4% | 8.0% |
|   | Perfume | 3.0% | 2.0% | 3.0% | 2.4% | 2.0% |
| B | Water | 24.0% | 34.0% | 24.0% | 29.2% | 34.0% |
|   | Appearance at 60 to 70° C. | inhomog. | inhomog. | ME-like | ME-like | ME-like |
|   | Dilution temperature | 40° C. | 40° C. | 40° C. | 40° C. | 40° C. |

|   |   | Impregnation emulsions | | | | |
|---|---|---|---|---|---|---|
|   |   | 1 Comparative example | 2 Comparative example | 3 | 4 | 5 |
| A | Polyglyceryl-2 dipolyhydroxystearate | 0.625% | 0.625% |   |   |   |
|   | Lauryl glucoside | 0.625% | 0.625% |   |   |   |
|   | Methyl glucose sesquistearate |   |   | 0.625% | 0.625% | 0.625% |
|   | Polyglyceryl-4 laurate |   |   | 0.625% | 0.625% | 0.625% |
|   | Ethylhexyl palmitate | 3.75% | 3.75% | 3.75% | 3.75% | 3.75% |
|   | Phenonip ® | 0.70% | 0.70% | 0.70% | 0.70% | 0.70% |
|   | Perfume | 0.20% | 0.20% | 0.20% | 0.20% | 0.20% |
|   | Water (total) | 94.10% | 94.10% | 94.10% | 94.10% |   |
|   | Appearance | inhomog. | inhomog. | finely divided | finely divided |   |
|   | Stability | unstable | unstable | stable | stable |   |

Emulsions 1 to 5:

Emulsions 1 to 5 show in particular that the emulsifier combination of polyglycerol-2 dipolyhydroxystearate and lauryl glucoside described in WO-A-02/056841 was not able to produce stable impregnation emulsions with the amount of alkyl paraben esters and phenoxyethanol (Phenonip®) (phenoxyethanol, methylparaben, ethylparaben, butylparaben, propylparaben isobutylparaben) required for adequate preservation of wet wipes. In comparison to this, it was found that an emulsifier combination according to the invention can successfully achieve this aim.

The impregnation emulsions shown in the table below were prepared by diluting the emulsion concentrates characterized in the table above (1 from 1a, 2 from 2a, etc.). As can be seen, the impregnation emulsions 1 and 2, and also 3, 4 and 5 were in each case identical. However, they were prepared via different emulsion concentrates.

It can be seen that using the combination of polyglyceryl-2 dipolyhydroxystearates and lauryl glucoside no microemulsion-like emulsion concentrates could be obtained whereas this was possible without problems using the emulsifier combinations according to the invention.

Accordingly, with this emulsifier combination it was also not possible to prepare impregnation emulsions having long-term stability with the required amount of the preservative Phenonip®.

Emulsions 6 to 9:

Using emulsions 6 to 9 it was shown that with the help of the emulsifier combination according to the invention which was also used in examples 3, 4 and 5, finely divided, low-viscosity impregnation emulsions according to the invention can also be prepared with many other oils. In this case too, the preparation was carried out by simply diluting the microemulsion-like emulsion concentrates (at about 40° C. with about 25° C.-hot water). The low-viscosity impregnation emulsions obtained were storage-stable for several months without further additives.

|   |   | Emulsion concentrate | | | |
|---|---|---|---|---|---|
|   |   | 6a | 7a | 8a | 9a |
| A | Methyl glucose sesquistearate | 7.5% | 7.5% | 7.5% | 7.5% |
|   | Polyglyceryl-4 laurate | 7.5% | 7.5% | 7.5% | 7.5% |
|   | Diethylhexyl carbonate | 45.0% |   |   |   |
|   | Decyl cocoate |   | 45.0% |   |   |
|   | Cetearyl ethylhexanoate |   |   | 45.0% |   |
|   | Isopropyl palmitate |   |   |   | 45.0% |
|   | Phenonip ® | 8.4% | 8.4% | 8.4% | 8.4% |
|   | Perfume | 2.4% | 2.4% | 2.4% | 2.4% |
| B | Water | 29.2% | 29.2% | 29.2% | 29.2% |
|   | Appearance at 60 to 70° C. | ME-like | ME-like | ME-like | ME-like |
|   | Dilution temperature | 40° C. | 40° C. | 40° C. | 45° C. |

|   | Impregnation emulsions | | | |
|---|---|---|---|---|
|   | 6 | 7 | 8 | 9 |
| Methyl glucose sesquistearate | 0.625% | 0.625% | 0.625% | 0.625% |
| Polyglyceryl-4 laurate | 0.625% | 0.625% | 0.625% | 0.625% |
| Diethylhexyl carbonate | 3.75% |   |   |   |
| Decyl cocoate |   | 3.75% |   |   |
| Cetearyl ethylhexanoate |   |   | 3.75% |   |
| Isopropyl palmitate |   |   |   | 3.75% |
| Phenonip ® | 0.7% | 0.7% | 0.7% | 0.7% |
| Perfume | 0.2% | 0.2% | 0.2% | 0.2% |
| Water (total) | 94.1% | 94.1% | 94.1% | 94.1% |
| Appearance | finely divided | finely divided | finely divided | finely divided |
| Stability | stable | stable | stable | stable |

Emulsions 10 to 13:

Emulsions 10 to 13 show that other polyglycerol partial esters could also be used to produce low-viscosity, finely divided oil-in-water emulsions. In the examples, only the composition of the impregnation emulsions was given. The preparation was carried out analogously to examples 1 to 9 via microemulsion-like emulsion concentrates at temperatures of from 50 to 80° C. and subsequent dilution with water.

|   | Impregnation emulsions | | | |
|---|---|---|---|---|
|   | 10 | 11 | 12 | 13 |
| Methyl glucose sesquistearate | 0.625% | 0.625% | 0.625% | 0.625% |
| Polyglyceryl-4 laurate* | 0.625% |   |   |   |
| Polyglyceryl-3 laurate* |   | 0.625% | 0.625% |   |
| Polyglyceryl-6 laurate* |   |   |   | 0.625% |
| Diethylhexyl carbonate |   |   | 3.75% |   |
| Isopropyl palmitate | 3.75% | 3.75% |   | 3.75% |
| Phenonip ® | 0.7% | 0.7% | 0.7% | 0.7% |
| Perfume | 0.2% | 0.2% | 0.2% | 0.2% |
| Water (total) | 94.1% | 94.1% | 94.1% | 94.1% |
| Appearance | finely divided | finely divided | finely divided | finely divided |
| Stability | stable | stable | stable | stable |

*The polyglyceryl-3/4/6 laurates used in these examples each had a degree of esterification of the polyglycerol of 20%.

Emulsions 14 to 17:

Using emulsions 14 to 17, it was shown that both different polyglycerol partial esters and also various emulsifiers based on carbohydrate could be used for preparing the impregnation emulsions according to the invention.

The preparation was carried out analogously to examples 1 to 13 via microemulsion-like emulsion concentrates at temperatures of from 50 to 80° C. and subsequent dilution with water.

|   | Impregnation emulsions | | | |
|---|---|---|---|---|
|   | 14 | 15 | 16 | 17 |
| Methyl glucose sesquistearate | 0.375% | 0.625% | 0.625% | 0.875% |
| Cetearyl glucoside | 0.625% |   |   |   |
| Polyglyceryl-4 laurate | 0.125% |   |   |   |
| Sorbitan monooleate |   | 0.625% | 0.583% |   |
| Polyglyceryl-4 caprate |   |   | 0.042% | 0.375% |
| Polyglyceryl-3 oleate |   |   |   | 0.250% |
| Diethylhexyl carbonate |   |   | 3.75% |   |
| Isopropyl palmitate |   | 3.75% |   |   |
| Ethylhexyl palmitate | 3.75% |   |   | 3.75% |
| Phenonip ® | 0.7% | 0.7% | 0.7% | 0.7% |
| Perfume | 0.2% | 0.2% | 0.2% | 0.2% |
| Water (total) | 94.1% | 94.1% | 94.1% | 93.85% |
| Appearance | finely divided | finely divided | finely divided | finely divided |
| Stability | stable | stable | stable | stable |

Cetearyl glucoside is the commercially available product TEGO ® Care CG 90 (Degussa), sorbitan monooleate is TEGO ® SMO V (Degussa), polyglyceryl-4 caprate is TEGOSOFT ® PC 41 (Degussa) and polyglyceryl-3 oleate is ISOLAN ® GO 33 (Degussa).

While the present invention has been particularly shown and described with respect to preferred embodiments thereof, it will be understood by those skilled in the art that the foregoing and other changes in forms and details may be made without departing from the spirit and scope of the present invention. It is therefore intended that the present invention not be limited to the exact forms and details described and illustrated, but fall within the scope of the appended claims.

What is claimed is:

1. An oil-in-water emulsion comprising a non-ethoxylated emulsifier combination including noncarbohydrate polyol partial esters of linear or branched fatty acids having 6 to 22 carbon atoms (emulsifier component A) and emulsifiers based on carbohydrate (emulsifier component B), one or more oils, and at least 10% by weight of preservative, based on the total amount of emulsifier components A and B.

2. The oil-in-water emulsion as claimed in claim 1, which comprises 20 to 75% by weight of preservative, based on the total amount of emulsifier components A and B.

3. The oil-in-water emulsion as claimed in claim 1, which additionally comprises coemulsifiers and customary auxiliaries and additives.

4. The oil-in-water emulsion as claimed in claim 1, wherein emulsifier component A comprises exclusively or partly polyglycerol partial esters which are obtainable by reacting polyglycerols with linear or branched fatty acids having 6 to 22 carbon atoms.

5. The oil-in-water emulsion as claimed in claim 4, wherein the polyglycerol mixture has an average degree of condensation of from 2 to 10.

6. The oil-in-water emulsion as claimed in claim 4, wherein the degree of esterification of the polyglycerol mixture is between 5 and 70%, based on the original hydroxyl groups of the polyol.

7. The oil-in-water emulsion as claimed in claim 1, wherein the emulsifier component A is formed partly or completely by sorbitan mono- and/or diesters of unsaturated and saturated fatty acids having 6 to 22 carbon atoms.

8. The oil-in-water emulsion as claimed in claim 7, wherein emulsifier component A comprises, besides one or more polyglycerol partial esters, up to 50% by weight of sorbitan esters, based on the total amount of emulsifier component A.

9. The oil-in-water emulsion as claimed in claim 1, wherein the emulsifier component B is selected from one or more of the following groups
   i) esters of mono- and/or polysaccharides and one or more linear or branched fatty acids having 6 to 22 carbon atoms,
   ii) glycosides of mono- or polysaccharides and linear or branched fatty alcohols having 6 to 22 carbon atoms,
   iii) glycosides which have additionally been etherified with linear or branched fatty alcohols having 1 to 22 carbon atoms, and
   iv) glycoside esters of mono- or polysaccharides and linear or branched fatty alcohols having 1 to 22 carbon atoms and one or more linear or branched fatty acids having 1 to 22 carbon atoms.

10. The oil-in-water emulsion as claimed in claim 1, wherein the emulsifier component B is an alkyl polyglycoside having, on average, 1 to 5 sugar units.

11. The oil-in-water emulsion as claimed in claim 1, wherein the emulsifier components A and B are used in a weight ratio of from 9:1 to 1:9.

12. The oil-in-water emulsion as claimed in claim 1, wherein the total amount of the emulsifier components A+B used, based on the amount of oil to be emulsified, is in a range from 15 to 70% by weight.

13. The oil-in-water emulsion as claimed in claim 1, wherein the total amount of oil phase (emulsifier+oil) is in the range from 1 to 25% by weight.

14. The oil-in-water emulsion as claimed in claim 1, wherein the preservatives comprise mixtures of alkyl paraben esters with phenoxyethanol.

15. A method of preparing finely divided, low-viscosity oil-in-water emulsions comprising providing an emulsion concentrate at a temperature of about 40° C. or above, and diluting said emulsion concentrate, said emulsion concentrate comprising an emulsifier combination of noncarbohydrate polyol partial esters of linear or branched fatty acids having 6 to 22 carbon atoms (emulsifier component A) and emulsifiers based on carbohydrate (emulsifier component B), one or more oils, and at least 10% by weight of preservative, based on the total amount of emulsifier components A and B.

16. The method as claimed in claim 15, wherein said emulsion concentrate has a 30 to 90% strength transparency.

17. The method as claimed in claim 15, wherein the emulsion concentrate is stirred into an initially charged water phase of from 20° C. to 50° C.

18. An essentially PEG-free, transparent concentrate in the range from 50° C. to 65° C., comprising 30 to 90% by weight of a PEG-free emulsifier combination of noncarbohydrate polyol partial esters of linear or branched fatty acids having 6 to 22 carbon atoms (emulsifier component A) and emulsifiers based on carbohydrate (emulsifier component B), one or more oils, and preservative.

19. The concentrate as claimed in claim 18, which comprises 15 to 70% by weight of the emulsifier combination.

20. A preparation comprising at least an emulsion concentrate comprising an emulsifier combination of noncarbohydrate polyol partial esters of linear or branched fatty acids having 6 to 22 carbon atoms (emulsifier component A) and emulsifiers based on carbohydrate (emulsifier component B), one or more oils, and at least 10% by weight of preservative, based on the total amount of emulsifier components A and B.

21. The preparation as claimed in claim 20, which is substantially free of polyethylene glycol.

* * * * *